United States Patent [19]
Woods et al.

[11] Patent Number: 5,645,593
[45] Date of Patent: Jul. 8, 1997

[54] PROSTHESIS COMPONENT

[75] Inventors: John Stephen Woods; Derek Redvers Cooper; Caradoc John Morgan Thomas, all of Cirencester, England

[73] Assignee: Corin Medical Limited, United Kingdom

[21] Appl. No.: 406,298

[22] Filed: Mar. 17, 1995

[30] Foreign Application Priority Data

Apr. 12, 1994 [GB] United Kingdom ............ 9407195

[51] Int. Cl.$^6$ ................... A61F 2/28; A61F 2/32
[52] U.S. Cl. ................. 623/16; 623/18; 623/22; 623/23
[58] Field of Search .................. 623/16–23

[56] References Cited

U.S. PATENT DOCUMENTS

| | | | |
|---|---|---|---|
| 4,673,409 | 6/1987 | Van Kampen | 623/23 |
| 4,883,491 | 11/1989 | Mallory et al. | 623/22 |
| 4,944,759 | 7/1990 | Mallory et al. | 623/22 |
| 5,007,931 | 4/1991 | Smith | 623/16 |
| 5,263,986 | 11/1993 | Noiles et al. | 623/22 |
| 5,373,621 | 12/1994 | Ducheyne et al. | 623/16 |
| 5,405,389 | 4/1995 | Contar et al. | 623/16 |

FOREIGN PATENT DOCUMENTS

| | | | |
|---|---|---|---|
| 2 142 830 | 1/1985 | United Kingdom . | |
| 2181354 | 10/1986 | United Kingdom . | |
| 2268408 | 12/1994 | United Kingdom | 623/22 |
| WO93/00870 | 1/1993 | WIPO . | |

Primary Examiner—David Isabella
Assistant Examiner—Francis K. Cuddihy
Attorney, Agent, or Firm—Levisohn, Lerner, Berger & Langsam

[57] ABSTRACT

A prosthesis component having a surface intended, in use, to come into contact with bone tissue, wherein at least part of the external surface is textured to provide an array of lands or peaks (12, 12') separated by troughs (14, 14'), the troughs (14, 14') containing particles (20, 20') embedded in a biocompatible bonding material. The embedded particles (20, 20') preferably fill the troughs (14, 14') up to the level of the lands or peaks (12, 12'). This means that bone ingrowth into the lands or peaks (12, 12') and into the embedded particles (20, 20') can take place simultaneously, thus forming a rapid permanent fixing between the component and the bone with a reduced risk of dislodging of the component due to shear stresses and an increased tensile strength between the component and the adjacent bone.

7 Claims, 1 Drawing Sheet

PROSTHESIS COMPONENT

FIELD OF THE INVENTION

The invention relates to a prosthesis component, particularly to an endoprosthesis component.

DESCRIPTION OF THE PRIOR ART

There are many different ways of affixing components of endoprostheses in place. Initially, the relevant component must be held in place by mechanical means such as stems, pegs, screws or cementing but, in order to achieve adequate permanent fixing, bone ingrowth at the interface between the component and the relevant bone must be encouraged. This can be achieved in a number of different ways, including applying to the surface of the component a textured surface consisting of lands or peaks separated by troughs which has been found to encourage bone ingrowth. An alternative arrangement is to sinter a layer of spherical beads or particles onto the smooth surface of the component so that the bone can grow into the sintered layer between the beads or particles.

The main disadvantage of the textured surface is that, whilst some bone ingrowth in the area of the lands or peaks is achieved relatively quickly, bone ingrowth into the troughs can take a substantial amount of time. This means that there may be a period of time during which the ingrowth is well established only at spaced intervals across the surface of the component. This amount of ingrowth may well prove insufficient under certain circumstances and could result in the endoprosthesis becoming dislodged.

Bone ingrowth into a sintered layer of beads or particles is usually more rapid and even than ingrowth into a textured surface. However, whilst the sintering process is designed to affix the beads or particles securely to the surface of the component, the beads or particles can be vulnerable to shear forces occurring between the component and the bone. Excessive shear forces can tear away some or all of the sintered beads or particles leaving areas of the component surface which are not permanently attached to the respective bone, thus creating third body wear particles and increasing the risk of the endoprosthesis becoming dislodged.

SUMMARY OF THE INVENTION

An object of the invention is to provide a prosthesis component having an improved bone-contacting surface which encourages rapid bone ingrowth over the entire surface area. A further object of the invention is to provide a prosthesis component having an improved bone-contacting surface which is not vulnerable to damage due to excessive shear forces occurring between the component and the adjacent bone.

The invention provides a prosthesis component as set out in claim 1 and a method of manufacturing a prosthesis component as set out in claim 11. Advantageous features of the component and method are set out in the subsidiary claims.

By filling the troughs between the lands or peaks with embedded particles, the bone adjacent the surface of the component can begin its ingrowth into the troughs between the lands or peaks simultaneously with the ingrowth into the lands or peaks. This ingrowth between the embedded particles at an early stage results in a continuous area over which firm fixing between the component and adjacent bone is quickly achieved. The fact that lands or peaks are arranged regularly between the troughs filled by the embedded particles means that rigid barriers occur regularly within the layer of embedded particles and extend from the floor of each trough to the upper surface of the layer. These rigid barriers provide effective resistance to any excessive shear forces occurring between the component and the adjacent bone which greatly reduces the risk of the component becoming dislodged. Also, because of the increased contact area between the embedded particles and the textured surface as compared to the comparative contact area with a non-textured surface, the tensile strength between the component and the adjacent bone is increased.

Embodiments of the invention will now be described by way of example only with reference to the accompanying drawings.

BRIEF DESCRIPTION OF THE DRAWINGS

FIG. 2b is a section taken on line II—II of FIG. 2a;

FIG. 3b is a plan view of the surface shown in FIG. 3a.

DESCRIPTION OF PREFERRED EMBODIMENTS

Figure 1:
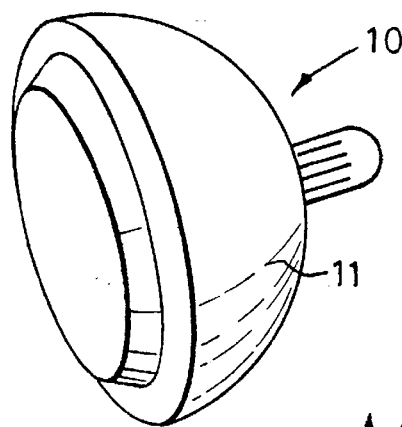
FIG. 1 shows an endoprosthesis component according to the invention.

FIG. 1 shows an endoprosthesis component 10, specifically an acetabular cup for a hip prosthesis, having a textured and sintered surface 11 according to the invention. The surface of the component 10 is shown in more detail in FIGS. 2a and 2b.

The surface of the component 10 is formed during manufacture with an array of lands 12 spaced apart in a regular manner by troughs 14. The array of lands 12 and troughs 14 can be applied to the surface of the component 10 at the end of the manufacturing process or as an integral part thereof. For example, the array can be cast into the surface or alternatively can be machined onto the surface using specific tools designed for the purpose in a known manner. The precise method by means of which the array of lands 12 and troughs 14 is applied to the surface of the component 10 does not form part of the present invention and therefore the process will not be described any further.

The resultant array consists of raised circular lands 12 of substantially 1.0 mm in diameter d separated by troughs 14 having a minimum bottom width w of substantially 0.7 mm. The upright walls 16 of the troughs 14 are inclined such that the minimum distance between the lower surfaces 18 of the troughs 14 is substantially 1.0 mm. The depth h of each trough is substantially 1.0 mm.

Between each land 12, the troughs 14 are filled with spherical beads 20 which are sintered to hold them securely in position. The beads 20 fill the troughs up to the level of the lands 12 but do not cover the lands 12, which remain exposed to contact with the adjacent bone when the component 10 is in use. The beads have an average diameter of substantially 0.2 mm and are manufactured from an implant grade Cobalt-Chrome alloy. The sintering material can be any one of a number of appropriate materials such as those already used to sinter a coating of beads onto a untextured component surface.

Figure 2A:
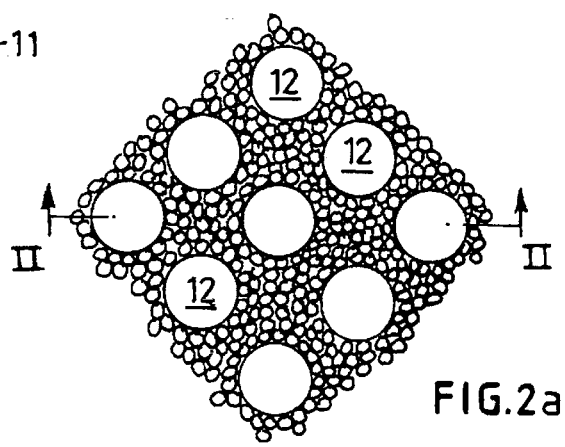
FIG. 2a is a plan view of a detail of the surface of the component of FIG. 1 shown on a highly enlarged scale.
Figure 2B:
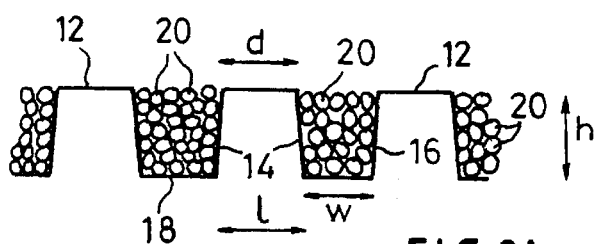

The surface illustrated in FIGS. 2a and 2b is advantageous because bone ingrowth is immediately possible into the lands 12 and into the areas of sintered beads 20 appearing between the lands 12. The bone ingrowth directly into the lands 12 forms a firm permanent fixing between the component 10 and the adjacent bone. Whilst this bone ingrowth is establishing itself, more rapid ingrowth can occur into the areas of sintered beads. However, because of the presence of the textured surface forming barriers of resistance to shear stresses throughout the layer of sintered beads 20, the sintered beads are not easily broken away or damaged due to stresses occurring between the component and the adjacent bone. The result is a rapid, permanent fixing of the component to the adjacent bone.

Figure 3A:
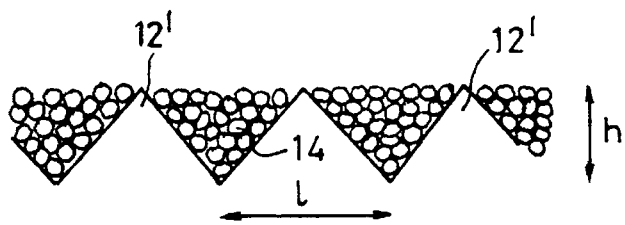
FIG. 3a is a sectional view of an alternative surface similar to that shown in FIG. 2b.
Figure 3B:
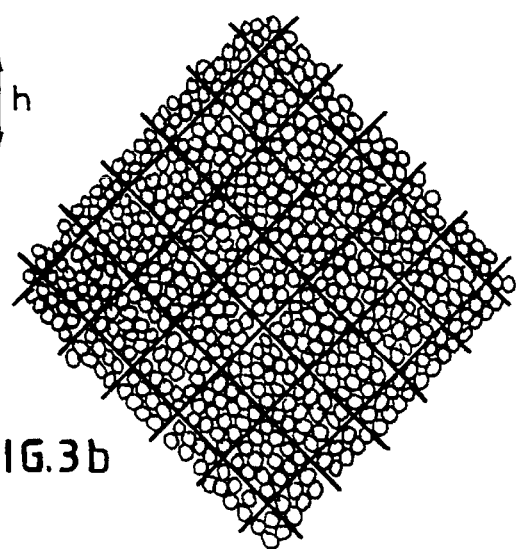

FIGS. 3a and 3b shows an alternative surface for an endoprosthesis component similar or identical to the component 10 shown in FIG. 1. In this alternative embodiment, the texture applied to the surface of the component consists of an array of pyramids or peaks 12' separated by troughs 14'. The height h' of each peak 12' above the floor of each trough 14' is again substantially 1.0 mm and the distance 1' between each trough is substantially 2.0 mm. Between each peak 12' sintered beads 20' are again located. The beads 20' are preferably similar or identical to these illustrated in FIG. 2a and 2b. Again, the beads 20' extend up to but do not cover the peaks 12'.

In this alternative embodiment, the area of the textured surface exposed directly to adjacent bone is greatly reduced. However, bone ingrowth into the upper regions of the peaks 12' is not hindered to any great extend by the presence of the sintered heads 20' and a sufficient area of ingrowth into the peaks 12' is rapidly achieved. In the meantime, ingrowth into the beads 20' located between the peaks 12' means that shear stresses occurring between the component and the adjacent bone do not result in large areas of sintered beads 20' becoming dislodged.

The method by which the textured surfaces described above are applied to the component will now be described. Initially, the textured surface consisting of the array of lands or peaks 12, 12' and troughs 14, 14' is created on the appropriate surface of the component. As mentioned above, there are several different known methods of applying such an array to the surface and any of these known methods could be used. Subsequently, the beads 20, 20' are introduced into the troughs 14, 14' and are sintered in place. This sintering process can involve introducing the beads 20, 20' and the sintering material into the troughs 14, 14' simultaneously or separately. When the beads 20, 20' and sintering material have been introduced into the troughs 14, 14', heat is applied to melt the sintering material and fix the beads 20, 20' in position.

The invention is not limited to the specific embodiments described above. Modifications and variations will be apparent to a reader skilled in the art. For example, the shape of the lands or peaks can be varied quite considerably. All that is required is that barriers of the surface material extend upwardly to the upper level of the sintered beads. The dimensions of the lands, peaks and troughs can also be varied to suit different requirements. Preferably, the average minimum distance between the peaks or troughs is between 0.5 mm and 5 mm. Also, the beads can be varied in size, the preferred range of average diameters being from 0.05 mm to 0.5 mm, and alternative embedding materials can be used if desired.

It is advantageous if the beads are all identical to one another but it is possible to use particles which are non-identical or irregular in shape and size. Materials other than Cobalt-Chrome alloys can be used as long as they are acceptable for use in implants. Bone ingrowth can be encouraged by coating the exposed surface of the component with Hydroxyapatite. Also, the textured surface described above can be applied to selected areas of the bone-contacting surface of the prosthesis component if desired or to fixing stems or pegs. It will also be understood that the textured surface described above can be applied to the bone-contacting surface of any and all types of prosthesis component; the invention is by no means limited in application to acetabular cups as illustrated in FIG. 1.

We claim:

1. A bone-contacting prosthesis component, comprising: a surface intended, in use, to come into contact with bone tissue, wherein at least part of said surface is textured to provide an array of lands separated by troughs, each of said lands being substantially circular, said troughs being depressions below the level of said lands and containing sintered particles embedded in a biocompatible bonding material such that said particles fill said troughs up to said level of said lands, said troughs each have sidewalls, said particles coating said sidewalls of said troughs, said array of lands serving to interrupt shear forces acting to shear away and dislodge said particles from said prosthesis component when said prosthesis component is in contact with bone tissue.

2. The prosthesis component of claim 1, wherein said particles are substantially spherical in shape.

3. A prosthesis component as claimed in claim 2, wherein said particles have an average diameter which is between about 0.05 mm and 0.5 mm.

4. The prosthesis component of claim 1, wherein said particles are made from a Cobalt-Chrome alloy.

5. The prosthesis component of claim 1, wherein said substantially circular lands are substantially 1 mm in diameter and height.

6. The prosthesis component is claimed in claim 5, wherein said prosthesis component has an average minimum distance between said lands which is between about 0.5 mm and 5 mm.

7. The prosthesis component of claim 6, wherein said prosthesis component has an average minimum distance between said lands which is substantially 1.3 mm.

* * * * *